US011964133B2

(12) United States Patent
Klemm et al.

(10) Patent No.: US 11,964,133 B2
(45) Date of Patent: Apr. 23, 2024

(54) SUPPLEMENTAL DEVICE FOR ATTACHMENT TO A PEN INJECTOR AND DETERMINATION OF A SET DOSE AMOUNT USING OPTICAL INCREMENTAL ENCODER

(71) Applicant: SANOFI-AVENTIS DEUTSCHLAND GMBH, Frankfurt am Main (DE)

(72) Inventors: Thomas Klemm, Frankfurt am Main (DE); Stefan Moessler, Berlin (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 395 days.

(21) Appl. No.: 16/987,019

(22) Filed: Aug. 6, 2020

(65) Prior Publication Data

US 2020/0360610 A1 Nov. 19, 2020

Related U.S. Application Data

(63) Continuation of application No. 15/545,043, filed as application No. PCT/EP2016/051245 on Jan. 21, 2016, now Pat. No. 10,737,029.

(30) Foreign Application Priority Data

Jan. 21, 2015 (EP) .................................... 15151912

(51) Int. Cl.
*A61M 5/24* (2006.01)
*A61M 5/31* (2006.01)
*A61M 5/315* (2006.01)
*G01F 23/292* (2006.01)

(52) U.S. Cl.
CPC .......... *A61M 5/24* (2013.01); *A61M 5/31525* (2013.01); *A61M 5/3155* (2013.01);
(Continued)

(58) Field of Classification Search
CPC .. A61M 5/24; A61M 5/31525; A61M 5/3155; A61M 2005/3126;
(Continued)

(56) References Cited

U.S. PATENT DOCUMENTS 2,685,083 A 7/1954 Beman
4,476,567 A 10/1984 Johnson
(Continued)

FOREIGN PATENT DOCUMENTS

JP H06-7741 2/1994
JP 2011-509783 3/2011
(Continued)

OTHER PUBLICATIONS

PCT International Preliminary Report on Patentability in International Appln. No. PCT/EP2016/051245, dated Jul. 25, 2017, 9 pages.

(Continued)

*Primary Examiner* — Theodore J Stigell
*Assistant Examiner* — Nidah Hussain
(74) *Attorney, Agent, or Firm* — Fish & Richardson P.C.

(57) ABSTRACT

A data collection device comprises at least two optical sensors configured to detect tick marks of a medicament dose indicator of the medicament delivery device in their respective detection areas, and a processing arrangement configured to determine a current medicament dosage programmed into said medicament delivery device based on a count of the tick marks that pass through the detection areas of the optical sensors during programming of said medicament dosage into said medicament delivery device. A direction of travel of the tick marks may be identified, to determine whether the programmed dosage is increasing or decreasing. The apparatus may be arranged to identify a baseline dosage amount using a camera image of the medi- (Continued)

cament dosage indicator, so that a starting point for the count of tick marks can be determined. The medicament delivery device may be an injector pen.

17 Claims, 8 Drawing Sheets

(52) U.S. Cl.
CPC ............... *A61M 2005/3126* (2013.01); *A61M 2205/3306* (2013.01); *A61M 2205/3561* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *G01F 23/292* (2013.01)

(58) Field of Classification Search
CPC .. A61M 2205/3306; A61M 2205/3561; A61M 2205/3569; A61M 2205/3584; A61M 2205/3592; A61M 2205/50; A61M 2205/502; A61M 5/31568; G01F 23/292
USPC ........................................................ 604/207
See application file for complete search history.

(56) References Cited

U.S. PATENT DOCUMENTS

| | | | |
|---|---|---|---|
| 6,380,536 B1 | 4/2002 | Inoue et al. | |
| 6,407,379 B1 | 6/2002 | Shinbo | |
| 10,471,213 B2 * | 11/2019 | Schabbach | A61M 5/31525 |
| 2012/0205528 A1 | 8/2012 | Augustyniak et al. | |
| 2015/0032059 A1 * | 1/2015 | Allerdings | A61M 5/31525 604/189 |
| 2015/0343152 A1 * | 12/2015 | Butler | A61M 5/31585 604/207 |

FOREIGN PATENT DOCUMENTS

| | | |
|---|---|---|
| JP | 2014-520584 | 8/2014 |
| JP | 2015-506770 | 3/2015 |
| JP | 2016-512966 | 5/2016 |
| WO | WO 2006/120182 | 11/2006 |
| WO | WO 2009/092807 | 7/2009 |
| WO | WO 2011/117212 | 9/2011 |
| WO | WO 2013/004844 | 1/2013 |
| WO | WO 2013/120777 | 8/2013 |
| WO | WO 2014/023763 | 2/2014 |
| WO | WO 2014/111340 | 7/2014 |
| WO | WO 2014/111341 | 7/2014 |
| WO | WO 2014/111343 | 7/2014 |

OTHER PUBLICATIONS

PCT International Search Report and Written Opinion in International Appln. No. PCT/EP2016/051245, dated Jun. 2, 2016, 12 pages.

* cited by examiner

SUPPLEMENTAL DEVICE FOR ATTACHMENT TO A PEN INJECTOR AND DETERMINATION OF A SET DOSE AMOUNT USING OPTICAL INCREMENTAL ENCODER

CROSS-REFERENCE TO RELATED APPLICATIONS

This application is a continuation of U.S. application Ser. No. 15/545,043, filed on Jul. 20, 2017, which is a U.S. national stage application under 35 USC § 371 of International Application No. PCT/EP2016/051245, filed on Jan. 21, 2016, which claims priority to European Patent Application No. 15151912.1, filed on Jan. 21, 2015, the entire contents of which are incorporated herein by reference.

TECHNICAL FIELD

The present disclosure relates to an data and method for collecting medicament dosage information from a medicament delivery device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dosage window or display of the insulin pen. The dose is then injected by inserting the needle into a suited skin portion and pressing an injection button of the insulin pen.

To be able to monitor insulin injection, for instance to prevent false handling of the insulin pen or to keep track of the doses already applied, it is desirable to measure information related to a condition and/or use of the injection device, for example, one or more of the injected insulin type, dose and timing of the injection, in a manner that is reliable and accurate.

WO2011/117212 A1 discloses an apparatus configured for releasable attachment to a medical device or for releasably receiving at least a part of the medical device, such as an injection pen. The apparatus comprises one or more optical sensors for determining information relating to a condition or use of the medical device, such as a dosage to be dispensed by the device, programmed into the device by a user using optical character recognition.

SUMMARY

According to one aspect, there is provided a data collection device configured to be attached to, or releasably receive at least part of, a medicament delivery device, the data collection device, said data collection device including at least two optical sensors, each arranged to detect light from a respective detection area, and a processing arrangement, wherein the optical sensors are configured to detect tick marks of a medicament dose indicator of the medicament delivery device in their respective detection areas, and the processing arrangement is configured to determine a current medicament dosage programmed into said medicament delivery device based on a count of the tick marks that pass through the detection areas of the optical sensors during programming of said medicament dosage into said medicament delivery device.

Since the dosage is determined automatically during its programming, a user of the medicament delivery device is not required to perform an additional action to cause recordal of the dosage. For instance, the user is not required to take an image of the medicament dose indicator specifically for recording the medicament dosage.

In addition, the processing required for determining the dosage using a "light barrier" type technique may be less complex when compared with devices that utilize a full optical character recognition algorithm, particularly as pre-processing to correct exposure levels and other parameters may not be needed.

Also, where a camera is provided in the data collection device, the technical requirements for that camera in terms of resolution and dynamic range may be less onerous compared to cameras in devices that rely fully on optical character recognition to determine a programmed dose. For example, a camera may be provided to capture an image of at least a part of the medicament dosage indicator to determine an initial medicament dosage displayed in the window corresponds to an expected baseline amount, such as zero units, so that the absolute value of the count is known with certainty. Such a determination may be based on identification of at least one character or marking shown in the image. Since there is an expected baseline amount, the processing arrangement may be configured to compare the captured image with a template corresponding to a predicted image of the dosage window when the expected baseline amount is displayed, to calibrate the count and/or confirm that the count of tick marks will begin with an appropriate initial value. If the captured image is not consistent with the template, an audible and/or visual alert may be generated.

Where a camera is provided, the data collection device may include a display for showing the dosage displayed by the medicament dosage indicator, since the data collection device, when attached to the medicament delivery device, may obscure the user's view of the medicament dosage window. In such an embodiment, the displayed dosages may be calculated based on the expected baseline amount plus a current count of tick marks detected. Determining the dosages to be displayed to the user in this manner can avoid the need for carry out a full optical character recognition process.

An order in which the sensors detect a tick mark passing through their respective detection areas may be used to determine a direction in which the tick mark is travelling. The direction of travel can then be used to determine whether the programmed dosage is being increased or decreased.

The data collection device may be configured to determine that the programmed dosage is not being changed if the outputs of the optical sensors are unchanged for a predetermined period of time.

The data collection device may be configured to be releasably attached to the medicament delivery device, to allow it to be reused with other medicament delivery devices. In a particular example, the medicament delivery device is a disposable injector pen, and the data collection device can be reused with a second injector pen, or switched between injector pens as needed.

This aspect also provides a medicament delivery system including any of the data collection devices discussed above, together with the medicament delivery device.

The medicament delivery device may be an injector pen. In particular, the medicament delivery device may be a disposable injector pen. However, in other embodiments, the data collection device may be configured for use with other medicament delivery devices.

According to another aspect, a method of collection dosage information from a medicament delivery device includes, using two optical sensors, detecting tick marks of a medicament dosage indicator of the medicament delivery device, where said tick marks are present in a respective detection area of the two optical sensors, counting the tick marks that pass through the detection area during programming of a medicament dosage into the medicament delivery device, and, using a processing arrangement, determining a current medicament dosage programmed into said medicament delivery device based on a result of said count.

The method may also include, using a processing arrangement, determining whether the current medicament dosage is increasing or decreasing, based on an order in which the optical sensors detect tick marks in said respective detection areas.

Alternatively, or additionally, the method may include determining an initial medicament dosage displayed by the medicament dosage indicator, wherein the processing arrangement is configured to calculate the current medicament dosage based on said initial medicament dosage and said count. In one example, determining an initial medicament dosage comprises capturing an image of at least a part of the medicament dosage indicator using a camera and identifying at least one character or mark in said image.

The method may include determining whether the count has changed within a predetermined time period and, if it is determined that the count has not changed during said predetermined time period, outputting an indication of a finalized medicament dosage programmed into the medicament delivery device, wherein said finalized medicament dosage corresponds to the current medicament dosage.

In some embodiments, the medicament delivery device is an injector pen. For example, the medicament delivery device may be a disposable injector pen for the delivery of insulin. However, the method may be used to collect dosage information from injector pens for delivering other medications or from other types of medicament delivery devices.

BRIEF DESCRIPTION OF THE FIGURES

Example embodiments of the present disclosure will now be described with reference to the accompanying figures, of which.

DETAILED DESCRIPTION

In the following, embodiments of the present disclosure will be described with reference to collecting data from an insulin injection device, such as Sanofi's SoloSTAR® pen. The present disclosure is however not limited to such application and may equally well be deployed with injection devices that eject other medicaments, or other types of medicament delivery devices, or in applications other than the collection of data from medicament delivery devices, as noted hereinabove.

Figure 1:
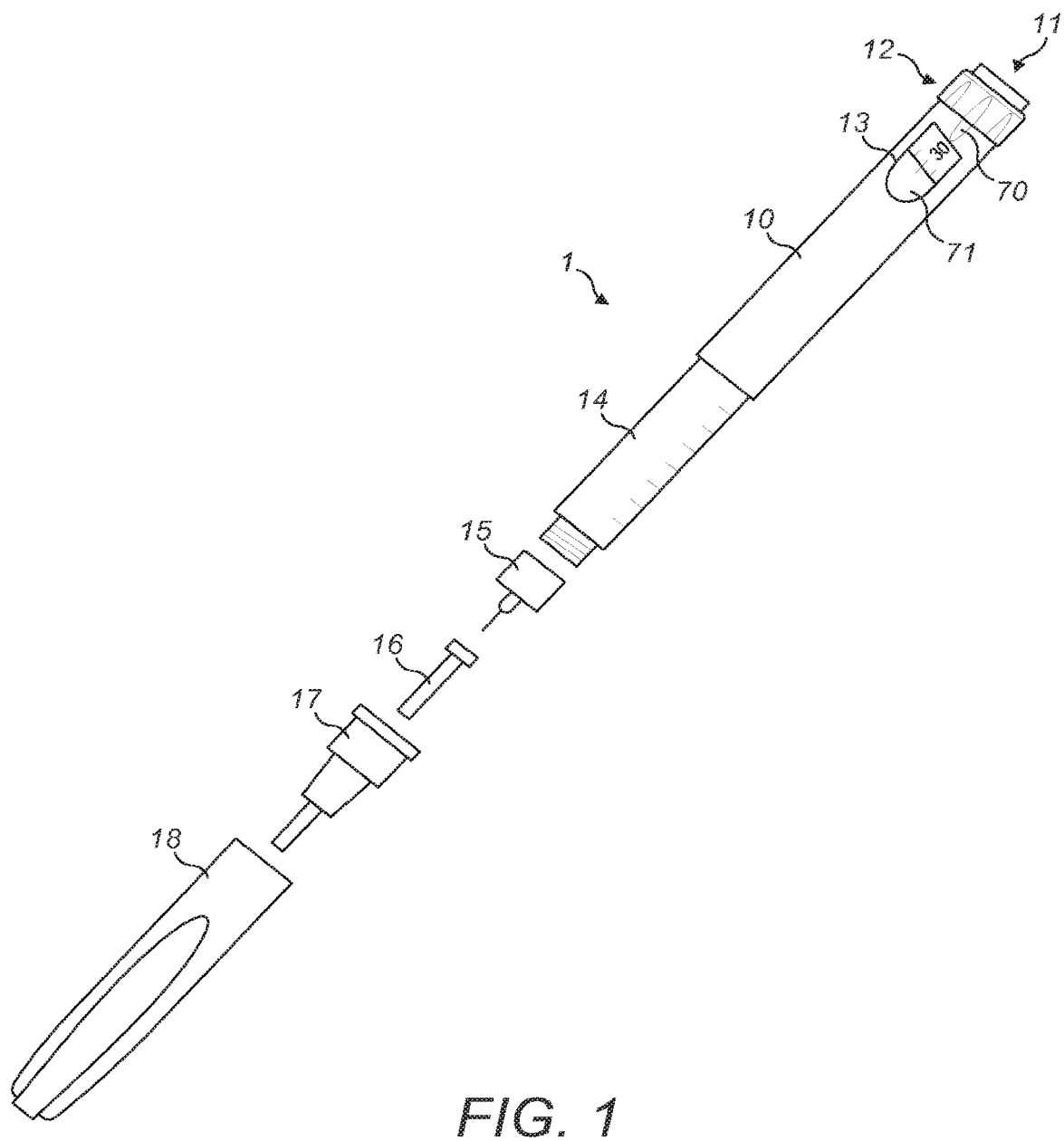
FIG. 1 is a perspective view of an example medicament delivery device from which dosage information may be collected.

FIG. 1 is an exploded view of a medicament delivery device. In this example, the medicament delivery device is an injection device 1, such as Sanofi's SoloSTAR® insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1. It should be noted that the selected dose may equally well be displayed differently.

The dosage window 13 may be in the form of an aperture in the housing 10, which permits a user to view a limited portion of a number sleeve 71 that is configured to move when the dosage knob 12 is turned.

Turning the dosage knob 12 causes a mechanical click sound to provide acoustic feedback to a user. The number sleeve 71 mechanically interacts with a piston in insulin container 14. When needle 15 is stuck into a skin portion of a patient, and then injection button 11 is pushed, the insulin dose displayed in the dosage window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 2:
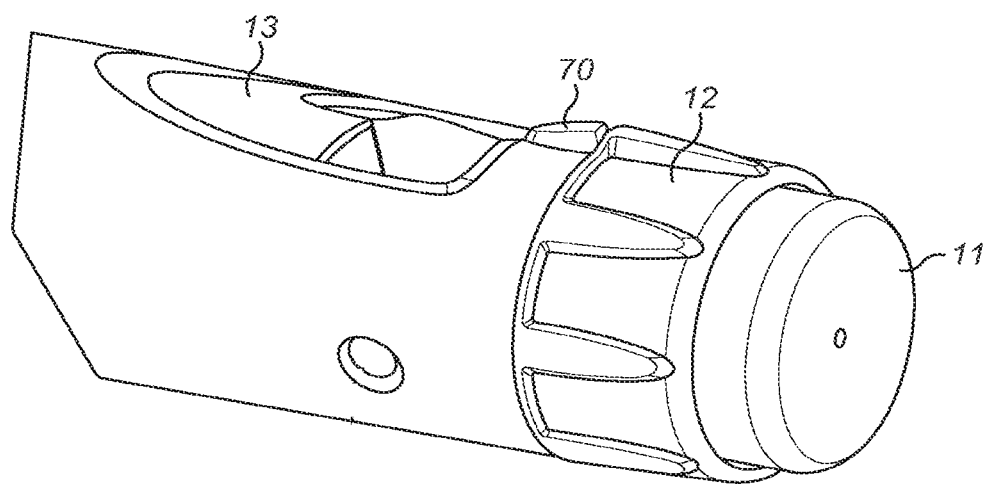
FIG. 2 is a detailed view of a portion of the medicament delivery device including a dosage window.

FIG. 2 is a close-up of the end of the injection device 1, showing a locating rib 70 that is located between the viewing window 13 and the dosage knob 12.

Figure 3:
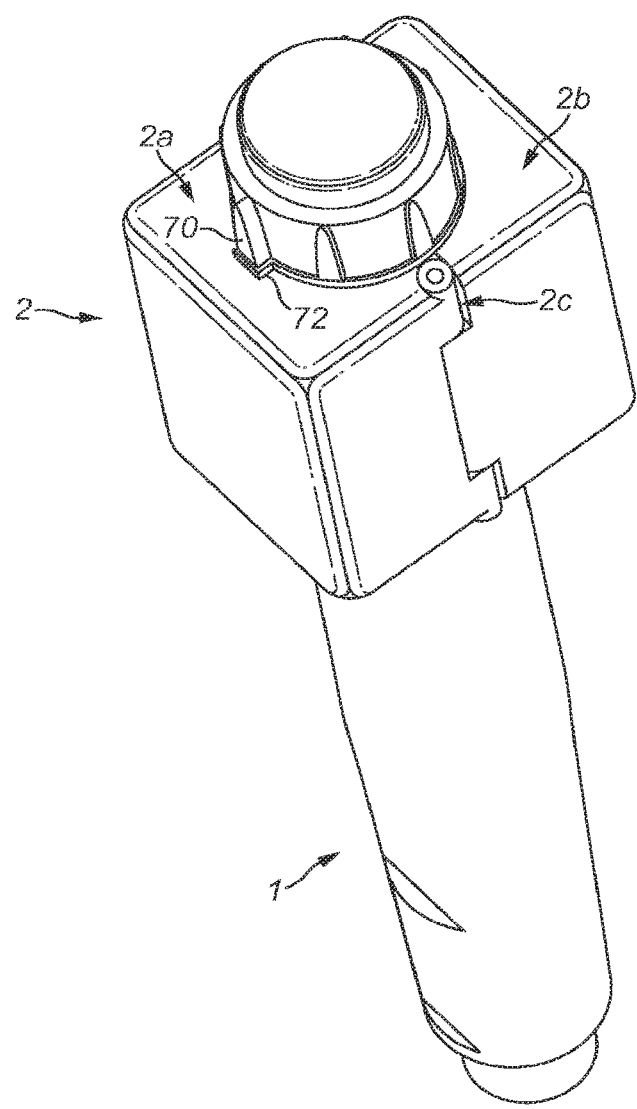
FIG. 3 is a perspective view of a data collection device according to an embodiment of the disclosure, attached to the medicament delivery device shown in FIG. 1.

FIG. 3 shows a data collection device 2 according to an embodiment of the disclosure, that may be used to collect dosage information when attached to the medicament delivery device 1.

In this particular embodiment, the data collection device 2 includes two housing portions 2a, 2b connected by a hinge 2c. The data collection device 2 is releasably attached to the medicament device 1 by placing a part of the medicament delivery device 1 into a recess in one of the housing portions 2a, 2b and closing the housing portions 2a, 2b together around the housing 10 of the medicament delivery device 1. The locating rib 70 interacts with a co-operating formation 72 on the data collection device so that the data collection device 2 is located at a suitable position on the medicament delivery device 1 to collect dosage information from the dosage window 13.

Figure 4:
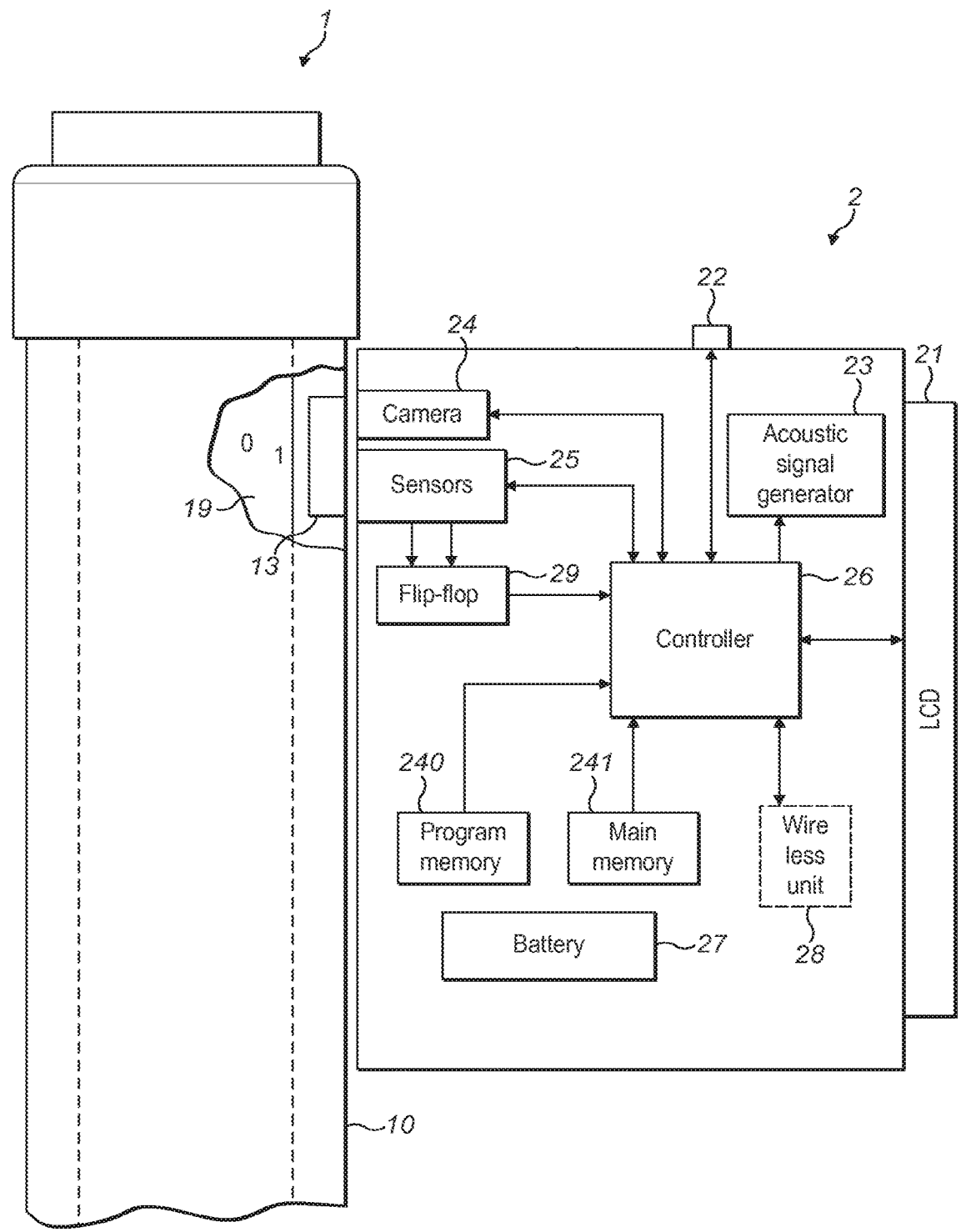
FIG. 4 is a block diagram showing components of the data collection device of FIG. 3.

FIG. 4 is a block diagram of the data collection device 2. In this particular example, the data collection device is equipped with two or more optical sensors 25 with an associated D flip-flop 29, a camera 24 and a controller 26. The controller 26 is a processing arrangement including one or more processors, such as a microprocessor, a Digital Signal Processor (DSP), Application Specific Integrated Circuit (ASIC), Field Programmable Gate Array (FPGA) or the like. The data collection device 20 also includes memory units 240, 241, including program memory 240 and main memory 241, which can store software for execution by the controller 26. The data collection device 20 also includes a wireless unit 28 to permit bi-directional communication over a network, such as a personal area network or Bluetooth® network, or a local wireless access network (WLAN). A display 21 and, optionally, an acoustical signal generator 23 are provided to allow visual and, if required, audio output. The data collection device 20 is powered by a battery 27 and a power button 22 is arranged to switch the device on and off.

For simplicity, the components of the data collection device 20 are shown in one block in FIG. 4. In the embodiment shown in FIG. 3, the components are divided between the housing portions 2a, 2b of the data collection device 20. For example, the display 21, the acoustical signal generator 23, where provided, and battery 27 may be provided in one of the housing portions 2a, while the controller 26, the optical sensors 25, the D flip-flop 29, the camera 24, the power button 22 and the wireless unit 28 may be provided in the other housing portion 2b.

However, the division of the components of the data collection device 20 are not limited to that particular configuration. In other embodiments, the housing portions 2a, 2b may include a different combination of the components than the combinations described herein.

Figure 5:
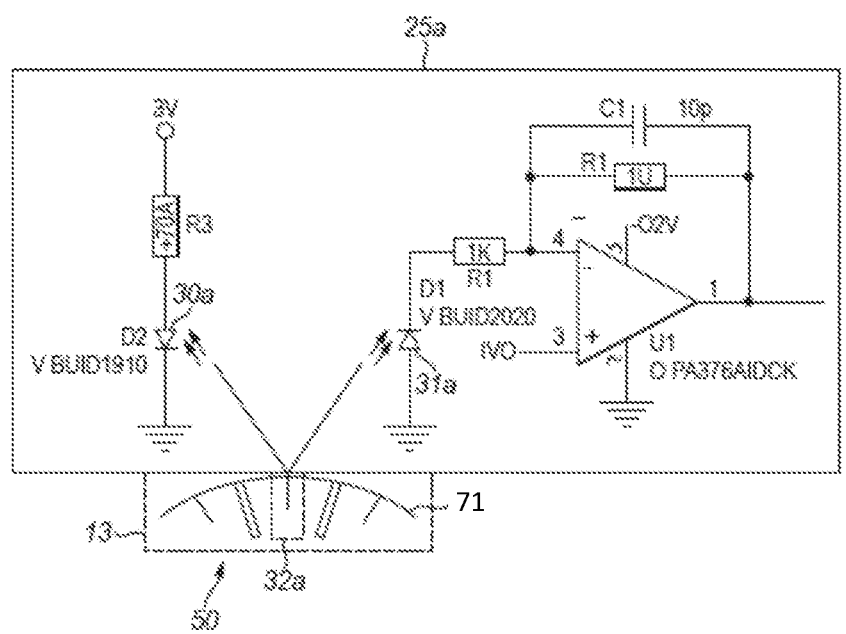
FIG. 5 depicts an example of an optical sensor that can be used in the data collection device of FIG. 3.

FIG. 5 is a circuit diagram of one optical sensor 25a in the data collection device 20 as an example. The optical sensor 25a includes a light source 30a, such as a light emitting diode (LED), and a photodetector 31a. In this particular example, the light source 30a emits infra-red (IR) radiation at a wavelength of 940 nm.

When the data collection device 20 is attached to the medicament delivery device 1, the optical sensor 25a is positioned over the dosage window 13 so that light emitted from the light source 30a is incident on tick marks 50 on the number sleeve 71 within a detection area 32a of the optical sensor 25a. Preferably, the housing portions 2a, 2b are configured to shield the detection area 32a from ambient light, to facilitate detection of the tick marks by the optical sensor 25a.

Light is reflected from the number sleeve 71 is received by the photodetector 31a. The intensity of the light received by the photodetector 31a at a particular moment indicates whether or not a tick mark 50 is present in the detection area 32a. In this particular example, the detection area 32a is configured with a narrow width and that the intensity of the received light increases as a tick mark 50 is moved through the detection area 32a and then decreases as the tick mark 50 leaves the detection area 32a, until the next tick mark enters the detection area 32a. In other embodiments, the intensity of light received by a sensor 25a may, instead, decrease as a tick mark 50 enters a detection area 32a, depending on the reflectivity of the tick marks relative to the background on the number sleeve 71.

Figure 6:
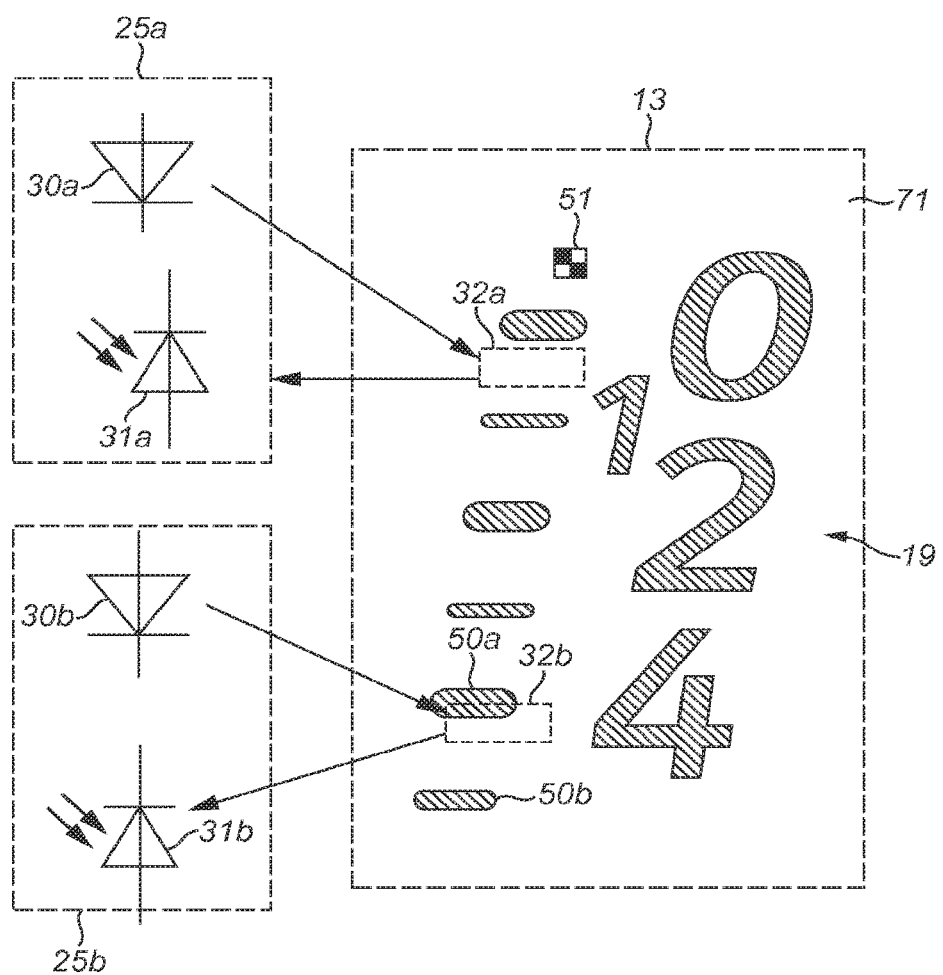
FIG. 6 shows an arrangement of two optical sensors in the data collection device of FIG. 3.

In this particular embodiment, two optical sensors 25a, 25b are provided, as shown in FIG. 6, each including a light source 30a, 30b and a photodetector 31a, 31b arranged to monitor a respective detection area 32a, 32b.

In FIG. 6, the detection areas 32a, 32b are shown as being separated, for clarity. However, in this particular embodiment, the detection areas 32a, 32b are arranged so that a tick mark 50 that is moved through the dosage window in a first direction will be detected by a first one of the optical sensors 25b as it moves into the detection area 32b for that sensor. As the dosage continues increasing, the tick mark 50 will move into the detection area 32a of the other optical sensor 25a. The example shown in FIG. 6 also includes a baseline detection marking 51 on the number sleeve 71, which can be used to determine whether a baseline dosage amount is shown in the dosage window 13.

Figure 7:
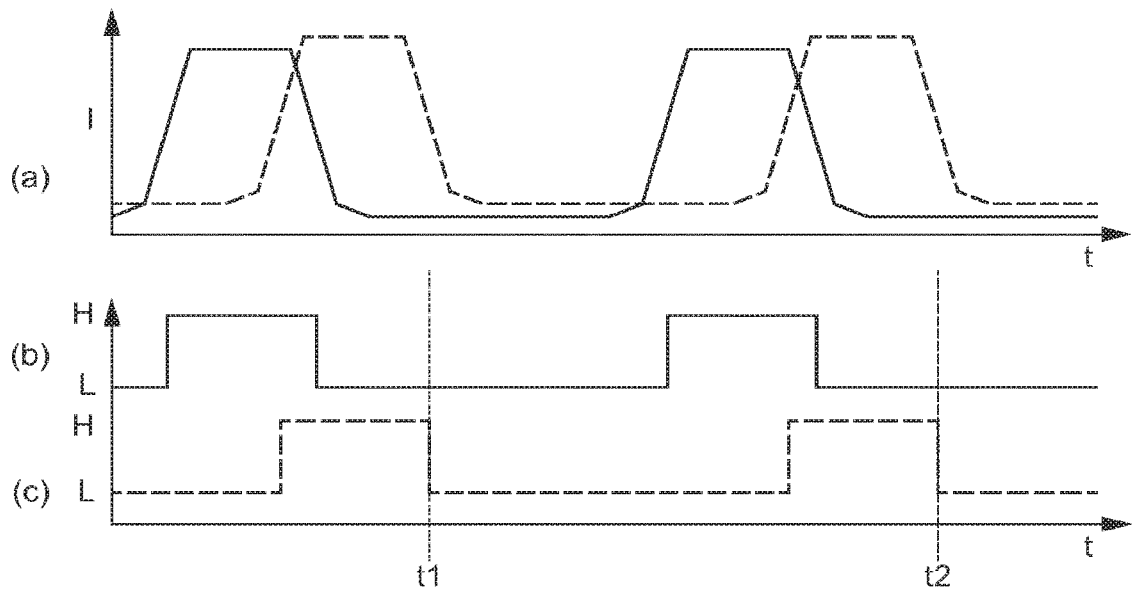
FIGS. 7 and 8 depict intensities of light received by the optical sensors and output signals from the optical sensors in the device of FIG. 1 as a dosage is programmed into the medicament delivery device.

FIG. 7, part (a) shows examples of the light intensities received by the optical sensors 25a, 25b, in an arrangement where the detection areas 32a, 32b are positioned closely as described above. As a user turns the knob 12 to increase the dosage, tick mark 50 enters the detection area 32b, the output of optical sensor 25b, shown as a solid line, increases and remains high until the tick mark 50a moves out of the detection area 32b. The received light intensity remains low until a subsequent tick mark 50b enters the detection area 32b.

Before the tick mark 50a leaves detection area 32b, its leading edge moves into detection area 32a and the intensity of light received by optical sensor 25a, shown as a dashed line, also increases until the tick mark 50a leaves the detection area 32a.

FIG. 7, parts (b) and (c) show signals output by the optical sensors 25a, 25b respectively. These signals have a high or low level depending on whether the intensity of the light received by those sensors 25a, 25b exceeds a predetermined threshold. The solid line depicts the output from sensor 25b, while the dashed line depicts the output from sensor 25a. In this particular embodiment, the count is increased when a trailing edge of each tick mark 50a, 50b leaves detection area 32a. The timings at which the count is increased are indicated as t1 and t2.

Figure 8:
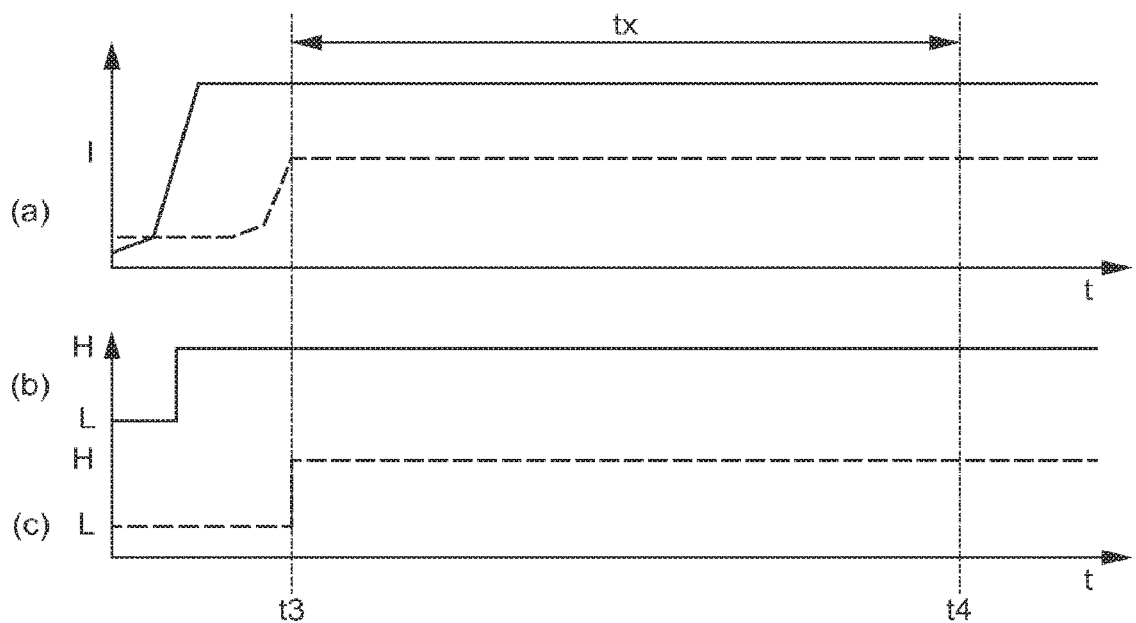

FIG. 8 depicts the received light intensities and optical sensor outputs in an example where the user completes the programming of the dosage at time t3. In this particular example, a tick mark is present in detection area 32b but has only just begun to enter detection area 32a. The controller 26 is configured to detect when a predetermined period of time tx has elapsed without a change in the output signals or, alternatively, in the count itself. In this example, time tx is set to 8 seconds.

At time t4, the time period tx has elapsed, and the controller 26 determines that the finalized medicament dosage is the initial dosage adjusted by the result of the count.

In addition to being used by the controller 26 for the count itself, the signals from the optical sensors 25a, 25b are provided as inputs to the D flip-flop 29. The output from the D flip-flop 29, based on the order in which rising edges of the signals from the optical sensors 25a, 25b are detected, will be a high level or a low level and, therefore depends on the direction in which the tick marks are moved. Hence, the controller 26 can determine the direction of travel and whether the medicament dosage is being increased or decreased, based on the output signal from the D flip-flop 29.

Figure 9:
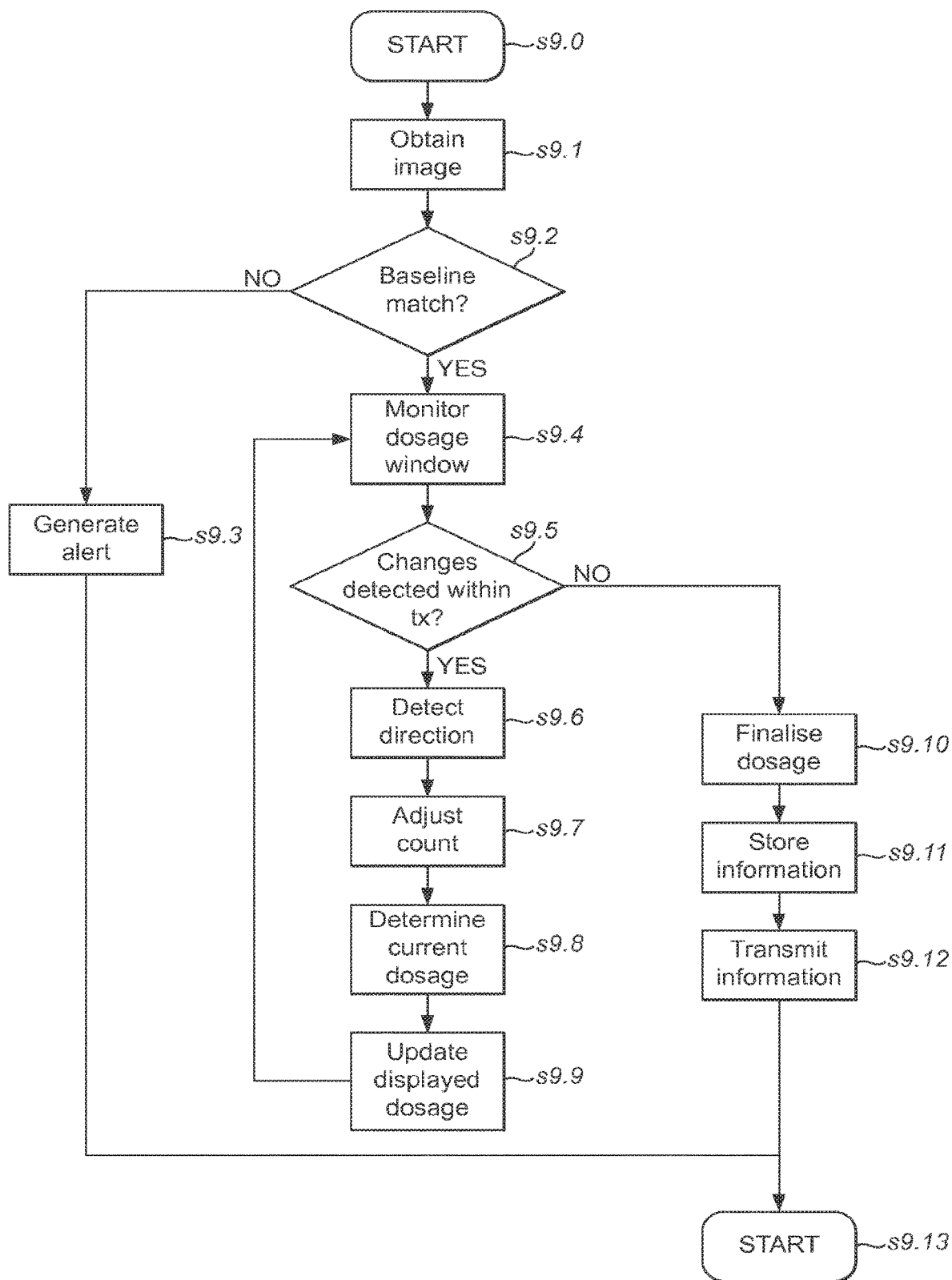
FIG. 9 is a flowchart of a method according to an embodiment of the disclosure.

A method of collecting dosage information will now be described, with reference to FIG. 9.

Starting at 9.0, the camera 24 is used to capture an image of at least part of the dosage window 13 (step s9.1).

This image is then processed by the controller 26 to determine whether the dosage currently displayed in the dosage window is an expected initial value (step s9.2). For example, some injector pens automatically reduce the number 19 displayed in the dosage window 13 to zero when an injection is administered, and so it would be expected that the initial value shown in the dosage window 13 before a user programs a dosage for a subsequent injection, should read zero or another expected baseline dosage amount, or display a character indicating the same. If this check is not made, then the actual dosage programmed into the injection pen 1 cannot be determined with certainty.

As noted above, in this particular example a baseline detection marking 51 is included on the number sleeve 71. The baseline detection marking 51 may be a pattern or other mark, such as a two-dimensional code that can be detected by the camera 24, where provided. The baseline detection marking 51 may be visible at optical wavelengths and/or visible at other wavelengths. In this particular example, the baseline detection marking 51 is printed onto the number sleeve 71 using ink that is visible at infra-red (IR) wavelengths and the camera 24 is configured to be sensitive to IR radiation reflected from the number sleeve 71 to detect the baseline detection marking 51. Since the position of the camera 24 relative to the dosage window 13 is fixed by the locating rib 70, the baseline detection marking 51 would be expected to appear at a particular position in an image captured by the camera 24 when the displayed dosage matches the expected baseline dosage amount. In the example shown in FIG. 6, the expected baseline dosage amount is zero IU.

Alternatively, or additionally, the determination of whether the medicament dosage initially shown in the dosage window 13 corresponds to the expected baseline dosage amount may use the numerical characters printed on the number sleeve 71. In one example, one or more of the visible characters is selected, for example, the character or characters having the greatest height. Pattern matching is performed, based on a template stored in the one of the memories 240, 241 of the data collection device 20 that corresponds to the expected baseline dosage. Since the position of the camera 24 relative to the dosage window 13 is fixed by the locating rib 70, the selected character should provide a reasonable for the template if it corresponds to the expected baseline dosage. The comparison may be made on a pixel-by-pixel basis, or using a feature recognition process or a vector comparison process, for example.

In another embodiment, the selected character may be identified using a more elaborate optical character recognition process.

The confirmation of the medicament dosage amount initially displayed in the dosage window 13 using a baseline detection marking 51 and/or recognition of the numerical characters on the number sleeve 71 can allow an actual value of the programmed dosage to be determined with certainty, without requiring the user to perform specific steps to calibrate the measurement to be made.

If it found that the dosage displayed in the dosage window 13 is not consistent with the expected baseline dosage (step s9.2), an alert message is generated and presented on the display 21 and/or as an audible alarm using the acoustical signal generator 23 (step s9.3).

If the displayed dosage is consistent with the expected baseline dosage (step s9.2), then the data collection device 20 begins to monitor the dosage window 13 using the optical sensors 25a, 25b (step s9.4) to detect tick marks 50 being moved through the detection areas 32a, 32b. If changes to the output of the optical sensors 25a, 25b are detected within the predetermined time period tx (step s9.5), then the output from the D flip-flop 29 is used to determine whether the dosage programmed into the injection pen 1 is being increased or decreased (step s9.6), as discussed herein above.

The count is then adjusted (step s9.7) and the current dosage is determined (step s9.8). The output of the display 21 is updated to show the newly determined current dosage (step s9.9).

Steps s9.4 to s9.9 are repeated, so that the count and the current dosage presented on the display 21 continue to be updated based on the detection of tick marks by the optical sensors 25a, 25b.

When the user has finished programming the dosage into the injection pen 1, the optical sensors 25a, 25b will not detect further changes. If time period tx has elapsed since previous changes in the optical sensors outputs (step s9.5) or, in an alternative embodiment, if there have been no changes to the count during the time period tx, then the current dosage is taken to be the final medicament dosage (step s9.10), that is, the dosage that will be administered by the user. In some embodiments, a message might be output using the display 21 and/or the acoustical signal generator 23 to prompt the user to confirm the final medicament dosage.

The final medicament dosage is then stored (step s9.11) in the program memory 240 and, optionally, transmitted to another device (step s9.12), such as a computer, tablet device or smartphone, using the wireless unit 28.

The data collection process then ends (step s9.13).

While the embodiments above have been described in disclosure relation to collecting data from an insulin injector pen, it is noted that embodiments of the disclosure may be used for other purposes, such as monitoring of injections of other medicaments or other medical processes.

The invention claimed is:
1. A data collection device configured to be attached to, or releasably receive at least part of, a medicament delivery device, the data collection device comprising:
   at least two optical sensors, the at least two optical sensors being arranged to detect light from respective detection areas; and
   a processor, wherein the at least two optical sensors are configured to detect light intensity reflected from a plurality of regions of a medicament dose indicator of the medicament delivery device in the respective detection areas, and wherein the processor is configured to determine a current medicament dosage programmed into the medicament delivery device based on a count of detected changes of light intensity as the plurality of regions pass through the respective detection areas of the at least two optical sensors during programming of the current medicament dosage into the medicament delivery device, and determine whether the current medicament dosage is increasing or decreasing, based on an order in which the at least two optical sensors detect the changes of light intensity as the plurality of regions pass through the respective detection areas.

2. The data collection device according to claim 1, wherein the plurality of regions of the medicament dose indicator comprise at least two regions of different reflectivity.

3. The data collection device according to claim 2, wherein the plurality of regions of the medicament dose indicator comprise marks and spaces between the marks.

4. The data collection device according to claim 1, wherein the processor is configured to determine an initial medicament dosage displayed by the medicament dose indicator, and wherein the processor is configured to calculate the current medicament dosage based on the initial medicament dosage and the changes of light intensity.

5. The data collection device according to claim 4, comprising a camera configured to capture an image of at least a part of the medicament dose indicator, wherein the processor is configured to determine the initial medicament dosage by identifying at least one character or mark shown in the image.

6. The data collection device according to claim 5, wherein the processor is configured to identify the at least one character or mark based on a stored template corresponding to an expected initial medicament dosage.

7. The data collection device according to claim 1, wherein the data collection device is configured to output an indication of the current medicament dosage in response to a detected change in light intensity.

8. The data collection device according to claim 1, wherein the processor is configured to determine whether the light intensity detected by either of the at least two optical sensors has changed within a predetermined time period and, if it is determined that the light intensity detected by either of the at least two optical sensors has not changed during the predetermined time period, output an indication of a finalized medicament dosage programmed into the medicament delivery device.

9. A medicament delivery system comprising:
a medicament delivery device; and
a data collection device comprising:
at least two optical sensors, the at least two optical sensors being arranged to detect light from respective detection areas, and
a processor,
wherein the at least two optical sensors are configured to detect light intensity reflected from a plurality of regions of a medicament dose indicator of the medicament delivery device in the respective detection areas, and wherein the processor is configured to determine a current medicament dosage programmed into the medicament delivery device based on a count of detected changes of light intensity as the plurality of regions pass through the respective detection areas of the at least two optical sensors during programming of the current medicament dosage into the medicament delivery device, and determine whether the current medicament dosage is increasing or decreasing, based on an order in which the at least two optical sensors detect the changes of light intensity as the plurality of regions pass through the respective detection areas.

10. The medicament delivery system according to claim 9, wherein the medicament delivery device comprises an injection device.

11. The medicament delivery system according to claim 10, wherein the injection device comprises a cartridge including a medicament, and the medicament comprises a pharmaceutically active compound.

12. A method of collecting dosage information from a medicament delivery device, the method comprising:

detecting, with at least two optical sensors, light intensity reflected from a plurality of regions of a medicament dosage indicator of the medicament delivery device, where the plurality of regions are present in respective detection areas of the at least two optical sensors;

detecting, with the at least two optical sensors, changes of light intensity as the plurality of regions pass through the respective detection areas of the at least two optical sensors;

determining, by a processor, a current medicament dosage programmed into the medicament delivery device based on a count of the changes of light intensity; and determining, by the processor, whether the current medicament dosage is increasing or decreasing, based on an order in which the at least two optical sensors detect the changes of light intensity as the plurality of regions pass through the respective detection areas.

13. The method according to claim 12, comprising determining an initial medicament dosage displayed by the medicament dosage indicator, wherein the processor is configured to calculate the current medicament dosage based on the initial medicament dosage and the changes of light intensity.

14. The method according to claim 13, wherein determining the initial medicament dosage comprises capturing an image of at least a part of the medicament dosage indicator using a camera and identifying at least one character or mark shown in the image.

15. The method according to claim 12, comprising determining whether the light intensity detected by either of the at least two optical sensors has changed within a predetermined time period and, if it is determined that the light intensity detected by either of the at least two optical sensors has not changed during said predetermined time period, outputting an indication of a finalized medicament dosage programmed into the medicament delivery device.

16. The method according to claim 12, wherein the medicament delivery device comprises an injection device.

17. The method according to claim 16, wherein the injection device comprises a cartridge including a medicament, and the medicament comprises a pharmaceutically active compound.

* * * * *